United States Patent
Meglan

(10) Patent No.: US 12,310,687 B2
(45) Date of Patent: *May 27, 2025

(54) GUIDANCE FOR POSITIONING A PATIENT AND SURGICAL ROBOT

(71) Applicant: Covidien LP, Mansfield, MA (US)

(72) Inventor: Dwight Meglan, Westwood, MA (US)

(73) Assignee: Covidien LP, Mansfield, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/589,942

(22) Filed: Feb. 28, 2024

(65) Prior Publication Data

US 2024/0197419 A1 Jun. 20, 2024

Related U.S. Application Data

(63) Continuation of application No. 16/960,476, filed as application No. PCT/US2019/012821 on Jan. 9, 2019, now Pat. No. 11,925,423.

(Continued)

(51) Int. Cl.
*G09B 23/28* (2006.01)
*A61B 34/00* (2016.01)
(Continued)

(52) U.S. Cl.
CPC .............. *A61B 34/30* (2016.02); *A61B 34/20* (2016.02); *A61B 34/25* (2016.02); *A61B 34/70* (2016.02);
(Continued)

(58) Field of Classification Search
CPC ......... A61B 34/30; A61B 34/20; A61B 34/25; A61B 34/70; A61B 90/36; A61B 90/50;
(Continued)

(56) References Cited

U.S. PATENT DOCUMENTS 8,878,900 B2 11/2014 Yang et al.
9,142,144 B2 * 9/2015 Meglan ................. G09B 23/30
(Continued)

FOREIGN PATENT DOCUMENTS

WO 2017083768 A1 5/2017

OTHER PUBLICATIONS

International Search Report dated Apr. 26, 2019 and Written Opinion completed Apr. 26, 2019 corresponding to counterpart Int'l Patent Application PCT/US2019/012821.
(Continued)

*Primary Examiner* — Eddy Saint-Vil
(74) *Attorney, Agent, or Firm* — Carter, DeLuca & Farrell LLP

(57) ABSTRACT

Systems, methods, and computer readable media for providing guidance for positioning a body and a surgical robot are disclosed. An exemplary system includes an image capture device configured to capture an image of a surgical training environment and generate image data of the surgical training environment, a head-mounted display, and a computing device configured to receive a surgical training parameter, receive the image data of the surgical training environment, detect a pose of the table and the surgical robot, generate a virtual training environment based on the surgical training environment, determine a pose of a user relative to the surgical training environment, generate guidance for positioning a body on the table or the surgical robot about the body, based on the surgical training parameter and the determined pose of the user, and cause the head-mounted display to display the generated guidance.

20 Claims, 6 Drawing Sheets

Related U.S. Application Data

(60) Provisional application No. 62/615,495, filed on Jan. 10, 2018.

(51) Int. Cl.
  *A61B 34/20* (2016.01)
  *A61B 34/30* (2016.01)
  *A61B 90/00* (2016.01)
  *A61B 90/50* (2016.01)

(52) U.S. Cl.
  CPC .............. *A61B 90/36* (2016.02); *A61B 90/50* (2016.02); *G09B 23/28* (2013.01); *A61B 2034/2065* (2016.02); *A61B 2034/252* (2016.02); *A61B 2034/306* (2016.02); *A61B 2090/365* (2016.02); *A61B 2090/371* (2016.02); *A61B 2090/372* (2016.02); *A61B 2090/502* (2016.02)

(58) Field of Classification Search
  CPC ...... A61B 2034/2065; A61B 2034/252; A61B 2034/306; A61B 2090/365; A61B 2090/371; A61B 2090/372; A61B 2090/502; G09B 23/28
  See application file for complete search history.

(56) References Cited

U.S. PATENT DOCUMENTS

| | | |
|---|---|---|
| 9,283,048 B2 | 3/2016 | Kostrzewski et al. |
| 2008/0306379 A1 | 12/2008 | Ikuma et al. |
| 2010/0248200 A1 | 9/2010 | Ladak et al. |
| 2011/0098553 A1 | 4/2011 | Robbins et al. |
| 2011/0306986 A1 | 12/2011 | Lee et al. |
| 2013/0196300 A1 | 8/2013 | Huang et al. |
| 2014/0098138 A1 | 4/2014 | Dogra et al. |
| 2014/0275760 A1 | 9/2014 | Lee et al. |
| 2016/0199147 A1 | 7/2016 | Shin |
| 2016/0331474 A1 | 11/2016 | Lacal et al. |
| 2018/0338806 A1 | 11/2018 | Grubbs |
| 2019/0008595 A1 | 1/2019 | Popovic et al. |

OTHER PUBLICATIONS

U.S. Appl. No. 62/615,481, filed Jan. 10, 2018, entitled "Guidance for Placement of Surgical Ports".

Extended European Search Report dated Aug. 4, 2021 corresponding to counterpart Patent Application EP 19738007.4.

* cited by examiner

GUIDANCE FOR POSITIONING A PATIENT AND SURGICAL ROBOT

CROSS-REFERENCE TO RELATED APPLICATIONS

This application is a Continuation Application which claims the benefit of and priority to U.S. patent application Ser. No. 16/960,476, filed on Jul. 7, 2020 (now U.S. Pat. No. 11,925,423), which is a National Stage Application of International Patent Application Serial No. PCT/US2019/012821, filed under 35 U.S.C. § 371 (a) and filed on Jan. 9, 2019, which claims the benefit of and priority to U.S. Provisional Patent Application Ser. No. 62/615,495, filed on Jan. 10, 2018, the disclosures of which are hereby incorporated by reference herein in their entireties.

BACKGROUND

Robotic surgery enables surgeons to perform various surgical procedures that would not be possible, or would be less efficient, by manual surgical techniques, such as open and/or laparoscopic surgical procedures. However, for surgeons to be comfortable using the surgical robot for robotic surgical procedures, extensive training and preparation is often required. One key aspect of preparing for robotic surgery involves preparing the surgical environment, such as placing the patient on the operating table and placing the various arms of the surgical robot about the patient. However, conventional training approaches for teaching a surgeon how to position a patient for a particular surgical procedure, and thereafter position the surgical robot about the patient to ensure best access to the surgical area, are quite time-consuming and, in some cases, even discourage adoption of robotic surgery systems. Disclosed hereinbelow are improved systems, apparatuses, methods, and computer-readable media for providing guidance and/or training for positioning a patient and a surgical robot for robotic surgery.

SUMMARY

The present disclosure relates to the provision of guidance for positioning patients and/or surgical robots, and more particularly, to systems, methods, and computer-readable media for generating and displaying virtual or augmented reality visual guidance to guide and/or train clinicians on how to position patients and/or one or more component(s) of a surgical robot for a variety of types of surgical robotic procedures.

Provided in accordance with an embodiment of the present disclosure is a system for providing guidance for positioning a body and a surgical robot. In an aspect of the present disclosure, the system includes an image capture device configured to capture an image of a surgical training environment including a table and a surgical robot, and generate image data of the surgical training environment based on the captured image; a head-mounted display (HMD) worn by a user; and a computing device including a processor and a memory storing instructions which, when executed by the processor, cause the computing device to receive a surgical training parameter, receive the image data of the surgical training environment from the image capture device, detect a pose of the table and the surgical robot based on the received image data, generate a virtual training environment based on the image data of the surgical training environment, the virtual environment including representations of the table and the surgical robot, determine a pose of the user relative to the surgical training environment based on the received image data and the generated virtual training environment, generate guidance for positioning at least one of at least a portion of a body on the table or at least a portion of the surgical robot about the body, based on the surgical training parameter and the determined pose of the user wearing the HMD relative to the surgical training environment, and cause the HMD to display the generated guidance.

In another aspect of the present disclosure, the body is a mannequin, and the surgical training environment further includes the body on the table.

In a further aspect of the present disclosure, the guidance includes a command for positioning at least a portion of the body on the table based on the surgical training parameter.

In yet a further aspect of the present disclosure, the command includes a textual command displayed by the HMD.

In still a further aspect of the present disclosure, the computing device causes the HMD to display an augmented reality image of a position of the at least one organ of the body as superimposed onto the body.

In another aspect of the present disclosure, the command includes an augmented reality image of a recommended position into which at least a portion of the body should be placed.

In a further aspect of the present disclosure, the guidance indicates when the user has placed at least a portion of the body into the recommended position.

In another aspect of the present disclosure, the guidance includes an augmented reality image of a position of at least one organ of the body.

In a further aspect of the present disclosure, the augmented reality image of the position of the at least one organ of the body is based on a model of positions of organs inside a patient's body.

In another aspect of the present disclosure, the command includes an augmented reality image of a recommended position into which at least a portion of the surgical robot should be placed.

In yet another aspect of the present disclosure, the virtual training environment further includes a representation of a virtual body.

In still another aspect of the present disclosure, the image capture device is coupled to the HMD.

In yet another aspect of the present disclosure, the image capture device is one of a plurality of image capture devices, and wherein the plurality of image capture devices are positioned at a plurality of respective positions about the surgical training environment.

In still another aspect of the present disclosure, the at least a portion of the surgical robot includes one or more of a base, a first joint, a first arm coupled to the first joint, a second joint coupled to the first arm, a second arm coupled to the second joint, and the base is coupled to the second arm by way of the first joint, first arm, and second joint.

In yet another aspect of the present disclosure, receiving the surgical training parameter includes loading a preconfigured surgical training parameter from the memory.

In still another aspect of the present disclosure, receiving the surgical training parameter includes receiving a selection of a surgical training parameter from input by a user.

In yet another aspect of the present disclosure, the surgical training parameter is based on a training program.

In a further aspect of the present disclosure, the training program is selected from a database of training programs.

In yet another aspect of the present disclosure, the database of training programs include training programs related to one or more of a type of surgery, a type of patient, a characteristic of the patient, and a type of medical condition being treated.

In a further aspect of the present disclosure, the training program is selected via a graphical user interface.

In another aspect of the present disclosure, the surgical training parameter includes one or more of a type of surgery, an age of a patient, a weight of the patient, a size of the patient, and a medical condition of the patient.

In yet another aspect of the present disclosure, the instructions for causing the computing device to determine a pose of the user wearing the HMD relative to the surgical training environment includes further instructions which, when executed by the processor, cause the computing device to analyze the received image data to identify the user and one or more of the table and the surgical robot in the received image data, determine a position of the user relative to one or more of the table and the surgical robot, and generate a representation of the user in the virtual environment based on the determined position of the user relative to one or more of the table or the surgical robot.

In still another aspect of the present disclosure, the instructions, when executed by the processor, further cause the computing device to determine whether the user has performed an action indicated by the guidance.

In a further aspect of the present disclosure, the image capture device is configured to capture additional image data of the surgical training environment, and wherein determining whether the user has performed the action indicated by the guidance includes analyzing the additional image data to detect a movement of the user, and determining, based on the detected movement of the user, whether the user has performed the action indicated by the guidance.

In yet a further aspect of the present disclosure, the instructions, when executed by the processor, further cause the computing device to determine a score based on the detected movement of the user, and cause the HMD to display the determined score.

Provided in accordance with an embodiment of the present disclosure is a method for providing guidance for positioning a body and a surgical robot. In an aspect of the present disclosure, the method includes receiving a selection of a surgical training parameter, obtaining image data of a surgical training environment including a table and a surgical robot, detecting a position of the table and the surgical robot based on the obtained image data, generating a virtual training environment based on the obtained image data of the surgical training environment, the virtual training environment including representations of the table and the surgical robot, determining a pose of a user wearing a head-mounted display device (HMD) relative to the surgical training environment based on the obtained image data and the generated virtual training environment, generating guidance for positioning at least one of at least a portion of a body on the table or at least a portion of the surgical robot about the body based on the surgical training parameter and the determined pose of the user relative to the surgical training environment, and causing the HMD to display the generated guidance.

In another aspect of the present disclosure, the body is a mannequin, and the surgical training environment further includes the body on the table.

In a further aspect of the present disclosure, the guidance includes a command for positioning at least a portion of the body on the table based on the surgical training parameter.

In yet a further aspect of the present disclosure, the command includes a textual command displayed by the HMD.

In still a further aspect of the present disclosure, the method further includes causing the HMD to display an augmented reality image of a position of the at least one organ of the body as superimposed onto the body.

In another aspect of the present disclosure, the command includes an augmented reality image of a recommended position into which at least a portion of the body should be placed.

In a further aspect of the present disclosure, the guidance indicates when the user has placed at least a portion of the body into the recommended position.

In another aspect of the present disclosure, the guidance includes an augmented reality image of a position of at least one organ of the body.

In a further aspect of the present disclosure, the augmented reality image of the position of the at least one organ of the body is based on a model of positions of organs inside a patient's body.

In another aspect of the present disclosure, the command includes an augmented reality image of a recommended position into which at least a portion of the surgical robot should be placed.

In yet another aspect of the present disclosure, the virtual training environment further includes a representation of a virtual body.

In still another aspect of the present disclosure, the surgical training parameter is based on a training program.

In a further aspect of the present disclosure, the training program is selected from a database of training programs.

In yet a further aspect of the present disclosure, the database of training programs include training programs related to one or more of a type of surgery, a type of patient, a characteristic of the patient, and a type of medical condition being treated.

In still a further aspect of the present disclosure, the training program is selected via a graphical user interface.

In another aspect of the present disclosure, the surgical training parameter includes one or more of a type of surgery, an age of a patient, a weight of the patient, a size of the patient, and a medical condition of the patient.

In yet another aspect of the present disclosure, determining a pose of the user wearing the HMD relative to the surgical training environment includes analyzing the received image data to identify the user and one or more of the table and the surgical robot in the received image data, determining a position of the user relative to one or more of the table and the surgical robot, and generating a representation of the user in the virtual environment based on the determined position of the user relative to one or more of the table or the surgical robot.

In still another aspect of the present disclosure, the method further includes determining whether the user has performed an action indicated by the guidance.

In a further aspect of the present disclosure, the method further includes capturing additional image data of the surgical training environment, and determining whether the user has performed the action indicated by the guidance includes analyzing the additional image data to detect a movement of the user, and determining, based on the detected movement of the user, whether the user has performed the action indicated by the guidance.

In yet a further aspect of the present disclosure, the method further includes determining a score based on the detected movement of the user, and causing the HMD to display the determined score.

Provided in accordance with an embodiment of the present disclosure is a non-transitory computer-readable storage medium including instructions which, when executed by a computer, cause the computer to receive a selection of a surgical training parameter, obtain image data of a surgical training environment including a table and a surgical robot, detect a position of the table and the surgical robot based on the obtained image data, generate a virtual training environment based on the obtained image data of the surgical training environment, the virtual training environment including representations of the table and the surgical robot, determine a pose of a user wearing a head-mounted display device (HMD) relative to the surgical training environment based on the obtained image data and the generated virtual training environment, generate guidance for positioning at least a portion of a body on the table and positioning at least a portion of the surgical robot about the body based on the surgical training parameters and the determined pose of the user relative to the surgical training environment, and cause the HMD to display the generated guidance.

In another aspect of the present disclosure, the body is a mannequin, and the surgical training environment further includes the body on the table.

In a further aspect of the present disclosure, the guidance includes a command for positioning at least a portion of the body on the table based on the surgical training parameter.

In yet a further aspect of the present disclosure, the command includes a textual command displayed by the HMD.

In still a further aspect of the present disclosure, the instructions, when executed by the processor, cause the computer to cause the HMD to display an augmented reality image of a position of the at least one organ of the body as superimposed onto the body.

In another aspect of the present disclosure, the command includes an augmented reality image of a recommended position into which at least a portion of the body should be placed.

In a further aspect of the present disclosure, the guidance indicates when the user has placed at least a portion of the body into the recommended position.

In another aspect of the present disclosure, the guidance includes an augmented reality image of a position of at least one organ of the body.

In a further aspect of the present disclosure, the augmented reality image of the position of the at least one organ of the body is based on a model of positions of organs inside a patient's body.

In another aspect of the present disclosure, the command includes an augmented reality image of a recommended position into which at least a portion of the surgical robot should be placed.

In yet another aspect of the present disclosure, the virtual training environment further includes a representation of a virtual body.

In still another aspect of the present disclosure, the surgical training parameter is based on a training program.

In a further aspect of the present disclosure, the training program is selected from a database of training programs.

In yet a further aspect of the present disclosure, the database of training programs include training programs related to one or more of a type of surgery, a type of patient, a characteristic of the patient, and a type of medical condition being treated.

In still a further aspect of the present disclosure, the training program is selected via a graphical user interface.

In another aspect of the present disclosure, the surgical training parameter includes one or more of a type of surgery, an age of a patient, a weight of the patient, a size of the patient, and a medical condition of the patient.

In yet another aspect of the present disclosure, determining a pose of the user wearing the HMD relative to the surgical training environment includes analyzing the received image data to identify the user and one or more of the table and the surgical robot in the received image data, determining a position of the user relative to one or more of the table and the surgical robot, and generating a representation of the user in the virtual environment based on the determined position of the user relative to one or more of the table or the surgical robot.

In another aspect of the present disclosure, the instructions, when executed by the processor, further cause the computer to determine whether the user has performed an action indicated by the guidance.

In a further aspect of the present disclosure, the instructions, when executed by the processor, further cause the computer to capture additional image data of the surgical training environment, and determining whether the user has performed the action indicated by the guidance includes analyzing the additional image data to detect a movement of the user, and determining, based on the detected movement of the user, whether the user has performed the action indicated by the guidance.

In yet a further aspect of the present disclosure, the instructions, when executed by the processor, further cause the computer to determine a score based on the detected movement of the user, and cause the HMD to display the determined score.

Any of the above aspects and embodiments of the present disclosure may be combined without departing from the scope of the present disclosure.

BRIEF DESCRIPTION OF THE DRAWINGS

Various aspects and features of the present disclosure are described hereinbelow with references to the drawings, wherein.

DETAILED DESCRIPTION

The present disclosure relates to systems, methods, and computer-readable media for providing guidance for positioning a body of a patient (or, in some examples, a non-human body-such as a mannequin, a virtual body, and/or the like—that is modeled based upon the body of the patient or of another test subject) and a surgical robot. More particularly, the present disclosure relates to instructing a user, such as a surgeon, nurse, technician, and/or other operating room staff (hereinafter referred to as a clinician), how to position the body on an operating room table, and how to position a surgical robot about the body, to ensure best access for surgical tools coupled to the surgical robot to a surgical site within the body. Various forms of visual and/or auditory guidance may be displayed and/or emitted by various display devices and/or speakers, including head-mounted displays, such as augmented reality headgear and/or virtual reality headgear, as well as projectors configured to display visual guidance on the body, the operating room table, and/or elsewhere about the operating room. The guidance may include one or more commands directing the clinician to move the body, or any part thereof, into a particular position on the operating room table, and then to position the various arms of the surgical robot about the body in some particular manner. Thus, the systems, methods, and computer-readable media disclosed herein may be used during training for robotic surgery and/or during actual robotic surgical procedures to assist with the positioning of a human patient and surgical robot in the operating room.

Figure 1:
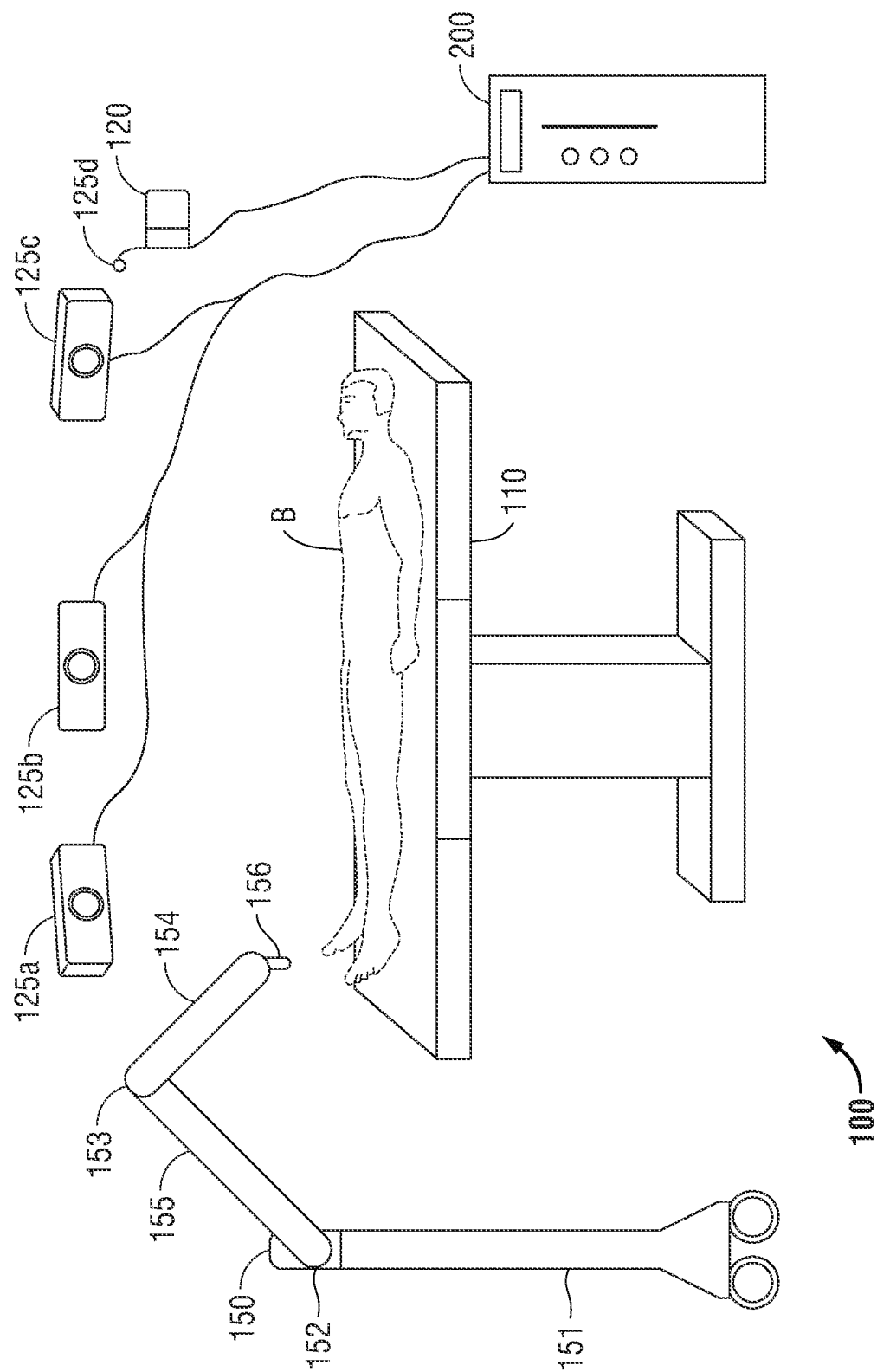
FIG. 1 is a schematic diagram of a system for providing guidance for positioning a patient and a surgical robot, according to an embodiment of the present disclosure.

With reference to FIG. 1, there is shown a system 100 for providing guidance for positioning a patient and a surgical robot, according to an embodiment of the present disclosure. System 100 may include a table 110 supporting a body B, a head-mounted display device (HMD) 120, one or more image capture devices 125a, 125b, 125c, and 125d, a surgical robot 150 including a robotic arm 155, and a computing device 200. HMD 120 may be any head-mounted display device configured to output augmented and/or virtual reality images. Image capture devices 125a, 125b, 125c, and 125d may be any image capture devices known to those skilled in the art, such as video cameras, still cameras, stereoscopic cameras, three-dimensional cameras including RGB-D cameras, LIDAR sensors, and/or the like, and may be positioned about a surgical training environment. One or more of the image capture devices 125a 125b, 125c, and 125d, for example image capture device 125d as shown in FIG. 1, may be included in or coupled to HMD 120. Additionally, or alternatively, image capture devices 125a, 125b, 125c, and 125d may be coupled or otherwise connected, whether by wireless or wired connection, to computing device 200. Image capture devices 125a, 125b, 125c, and 125d are referred to collectively hereinafter as image capture devices 125.

In addition to robotic arm 155, surgical robot 150 may further include a base 151, a first joint 152 coupled to base 151, a first robotic arm, such as robotic arm 155, coupled to first joint 152, a second joint 153 coupled to first robotic arm 155, a second arm 154 coupled to second joint 153, and an instrument drive unit 156 coupled to second arm 154. While surgical robot 150 is shown in FIG. 1 as a single robotic assembly, multiple robotic assemblies may be included in the surgical training environment, and those skilled in the art will recognize that the below-described methods may be applied to surgical robots 150 having single and/or multiple robotic assemblies, each including at least one base 151, robotic arms 154 and 155, joints 152 and 153, and instrument drive unit 156, without departing from the scope of the present disclosure. Body B may be a human body, such as a body of a patient, a non-human body, such as a mannequin or other simulated body, and/or a virtual body, which, in some cases is modeled based upon a human body of the patient or of a test subject. For example, in embodiments where body B is a virtual body, body B may be generated based on parameters of a particular patient and/or a test subject, and may be stored in computing device 200 to be loaded during a training procedure. In embodiments where body B is a virtual body, body B will not be physically present on table 110 in the surgical training environment, but will be displayed in the virtual training environment, as described below. Further, in embodiments where body B is a virtual body, table 110 may also be a virtual table generated by computing device 200 and/or HMD 120 and displayed via HMD 120.

Computing device 200 may be any computing device configurable for use during training for robotic surgery known to those skilled in the art. For example, computing device 200 may be a desktop computer, laptop computer, server and terminal configuration, and/or a control computer for surgical robot 150, and/or the like. In some embodiments, computing device 200 may be included in HMD 120. As described further below, system 100 may be used during training for robotic surgery, such as training for how to position body B on table 110 and how to position surgical robot 150 about body B.

Figure 2:
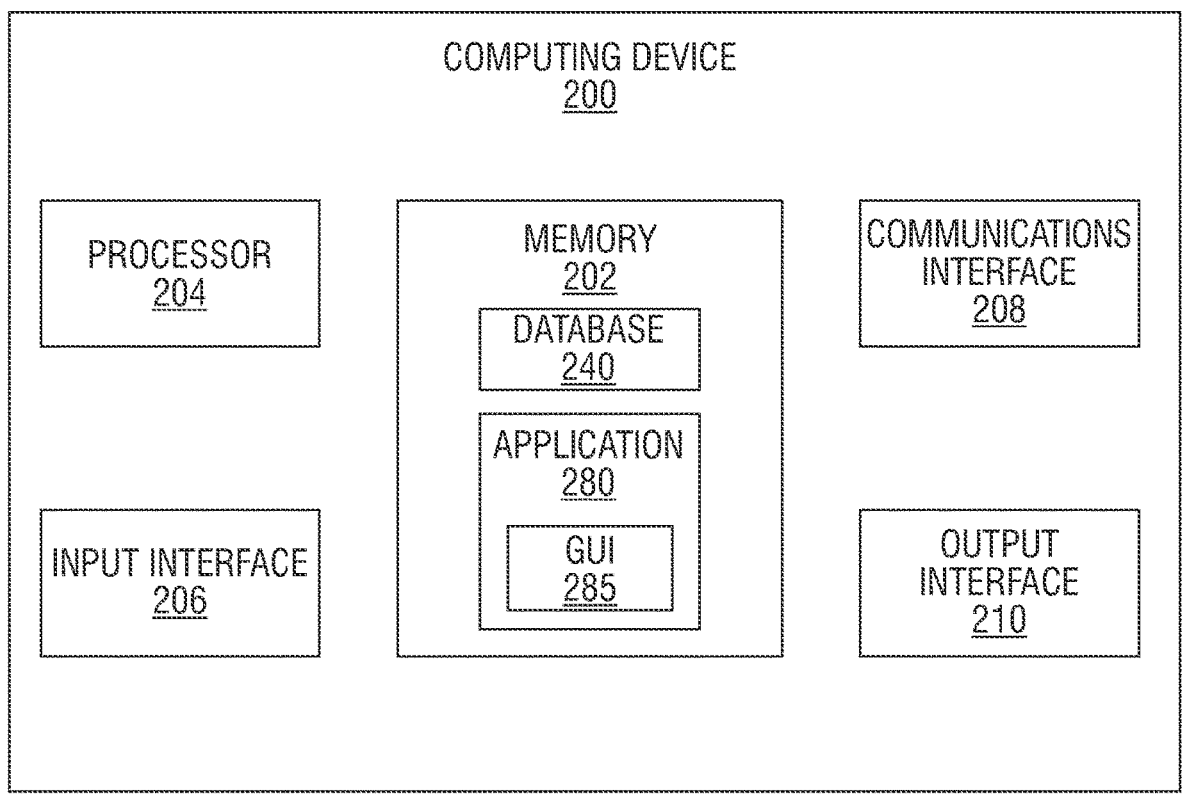
FIG. 2 is a block diagram of an exemplary computing device forming part of the system of FIG. 1.

Turning now to FIG. 2, there is shown a schematic diagram of computing device 200 forming part of system 100 of FIG. 1, according to an embodiment of the present disclosure. Computing device 200 includes a memory 202, a processor 204, an input interface 206, a communications interface 208, and an output interface 210. Memory 202 stores a database 240 and an application 280. Application 280 includes instructions that, when executed by processor 204, cause computing device 200 to perform various functions, as described below. Application 280 further includes graphical user interface (GUI) instructions 285 which, when executed by processor 204, cause computing device 200 to generate one or more GUIs (not shown in FIG. 2), such as, for example, the example GUI shown in FIG. 4. Database 240 stores various training programs including various surgical training parameters.

A training program is a set of commands designed to instruct a user to prepare an operating environment, as simulated by the surgical training environment, for robotic surgery. For example, the training program may include commands instructing the user to place and/or adjust a position of body B on table 110, place and/or adjust a position of surgical robot 150 relative to body B and/or table 110, and/or adjust a pose of surgical robot 150 relative to body B. The training program may include various steps and/or phases, each with its own set of commands. For example, each step and/or phase of the training program may include one or more commands instructing the user to perform a different action to prepare the operating environment for robotic surgery. A first step or phase may be directed to positioning body B on table 110, a second step or phase may be directed to adjusting the position of body B on table 110 to ensure best access to the surgical site, a third step or phase may be directed to placing surgical robot 150 about body B and/or table 110, and a fourth step or phase may be directed to adjusting the pose of surgical robot 150 relative to body B.

As used herein, the term "pose" is defined as a position and an orientation of an object. For example, the pose of surgical robot 150 refers to a position of surgical robot 150 within the surgical training environment, an orientation of surgical robot 150 with respect to the surgical training environment and other objects in the surgical training environment, and/or the configuration of one or more of base 151, robotic arms 154 and 155, joints 152 and 153, and instrument drive unit 156. Similarly, a pose of other objects in the surgical training environment, such as table 110 and body B, etc., may also be determined.

In some embodiments, multiple users may be trained concurrently, such as to perform different tasks to prepare an operating environment for robotic surgery. Each user may wear a HMD 120 configured to generate and display guidance for their respective portions of the training program. In such embodiments, the training program may include commands directed to each individual user to instruct each user to perform various steps and/or tasks assigned to them. The training program may further sequence the commands directed to each user to teach the various users how to perform their respective tasks as well as the order in which the various tasks should be performed when one user's task depends on another user first finishing their task. In other embodiments, some or all of the users may not wear a HMD 120, and the guidance may instead be displayed by a projector that displays the guidance directly onto body B, table 110, and/or elsewhere about the surgical training environment.

The surgical training parameters include various types of surgery, types of patients, characteristics of the patients, types of medical conditions being treated by the surgery, locations of surgical sites within the patient's body, and/or recommended positions of surgical ports on the patient's body to access the surgical sites. In some embodiments, one or more of the surgical training parameters may be dependent on and/or derived from another surgical parameter. For example, if the user selects "appendectomy" as the type of surgery, the location of the surgical site may be derived as the "lower abdomen." Likewise, recommended positions of surgical ports may be determined based on the type of surgery selected, and the location of the surgical site. Similarly, a recommended pose of surgical robot 150 may be determined based on the location of the surgical site and/or the recommended positions of surgical ports, and thus the commands instructing the user how to position and/or adjust the pose of surgical robot 150 may depend on and/or be determined based on the location of the surgical site and/or the recommended positions of surgical ports on body B. The characteristics of the patients include height, weight, bodytype, pre-existing medical conditions and/or surgeries previously performed on the patients, and/or other attributes of the patients. In embodiments, the training program and/or commands may be based on the surgical training parameters. Thus, the guidance displayed by HMD 120, as further described below, may include visual representations of the surgical sites and/or the recommended positions of surgical ports.

Memory 202 may include any non-transitory computer-readable storage medium for storing data and/or software that is executable by processor 204 and which controls the operation of computing device 200. In an embodiment, memory 202 may include one or more solid-state storage devices such as flash memory chips. Alternatively, or in addition to the one or more solid-state storage devices, memory 202 may include one or more mass storage devices connected to the processor 204 through a mass storage controller (not shown in FIG. 2) and a communications bus (not shown in FIG. 2). Although the description of computer-readable media included herein refers to a solid-state storage, it should be appreciated by those skilled in the art that computer-readable storage media can be any available media that can be accessed by processor 204. That is, computer-readable storage media may include non-transitory, volatile and non-volatile, removable and non-removable media implemented in any method or technology for storage of information such as computer-readable instructions, data structures, program modules, or other data. For example, computer-readable storage media may include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 200.

Input interface 206 may be a mouse, keyboard, or other hand-held controller, foot pedal, touch screen, voice interface, and/or any other device or interface by means of which a user may interact with computing device 200. Communications interface 208 may be configured to connect to a network such as a local area network (LAN) consisting of a wired network and/or a wireless network, a wide area network (WAN), a wireless mobile network, a Bluetooth network, and/or the internet. Output interface 210 may be a screen or other display device usable to output images or data by computing device 200.

Figure 3A:
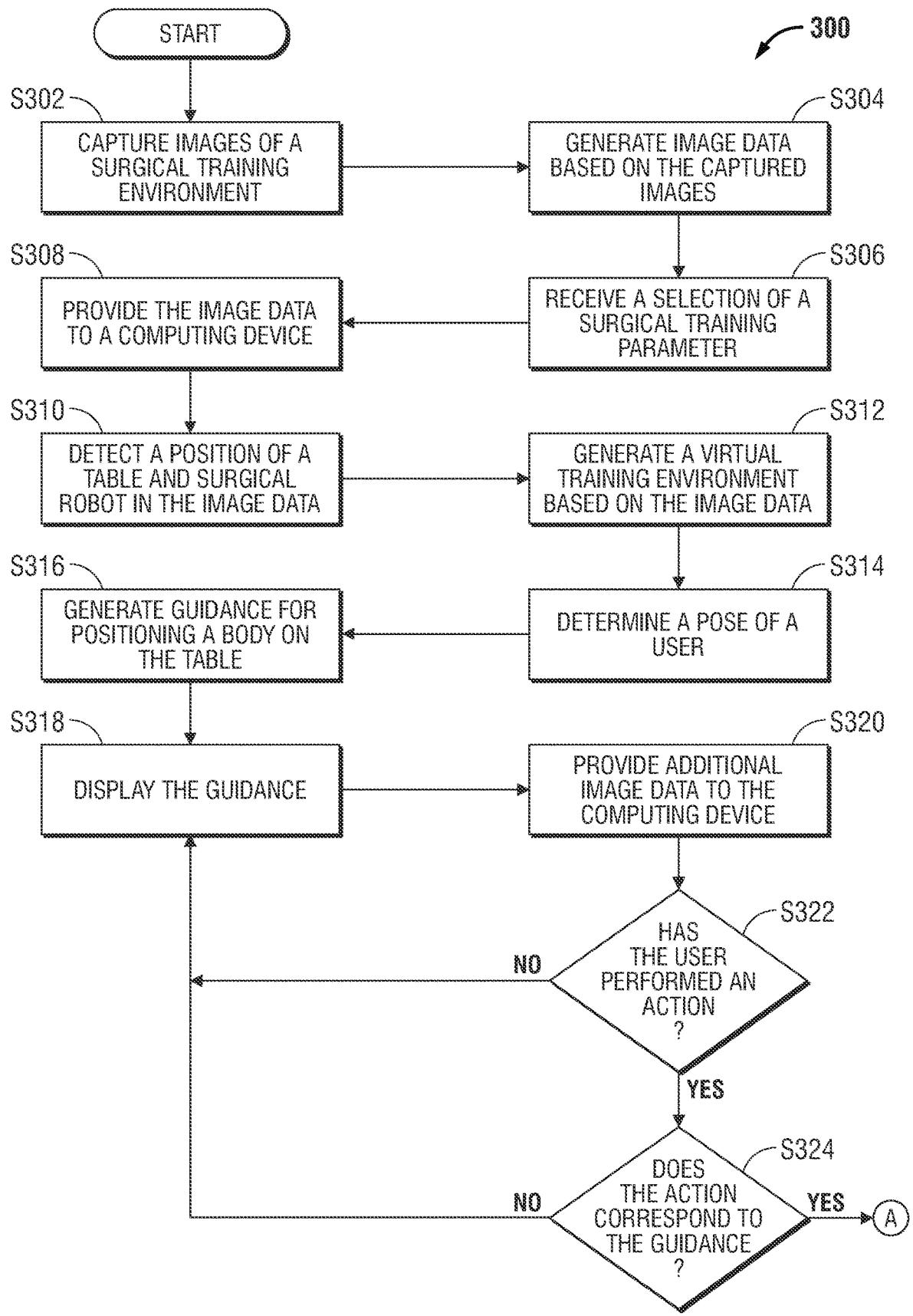
FIGS. 3A and 3B show a flowchart of an exemplary method for providing guidance for positioning a patient and a surgical robot, according to an embodiment of the present disclosure.
Figure 3B:
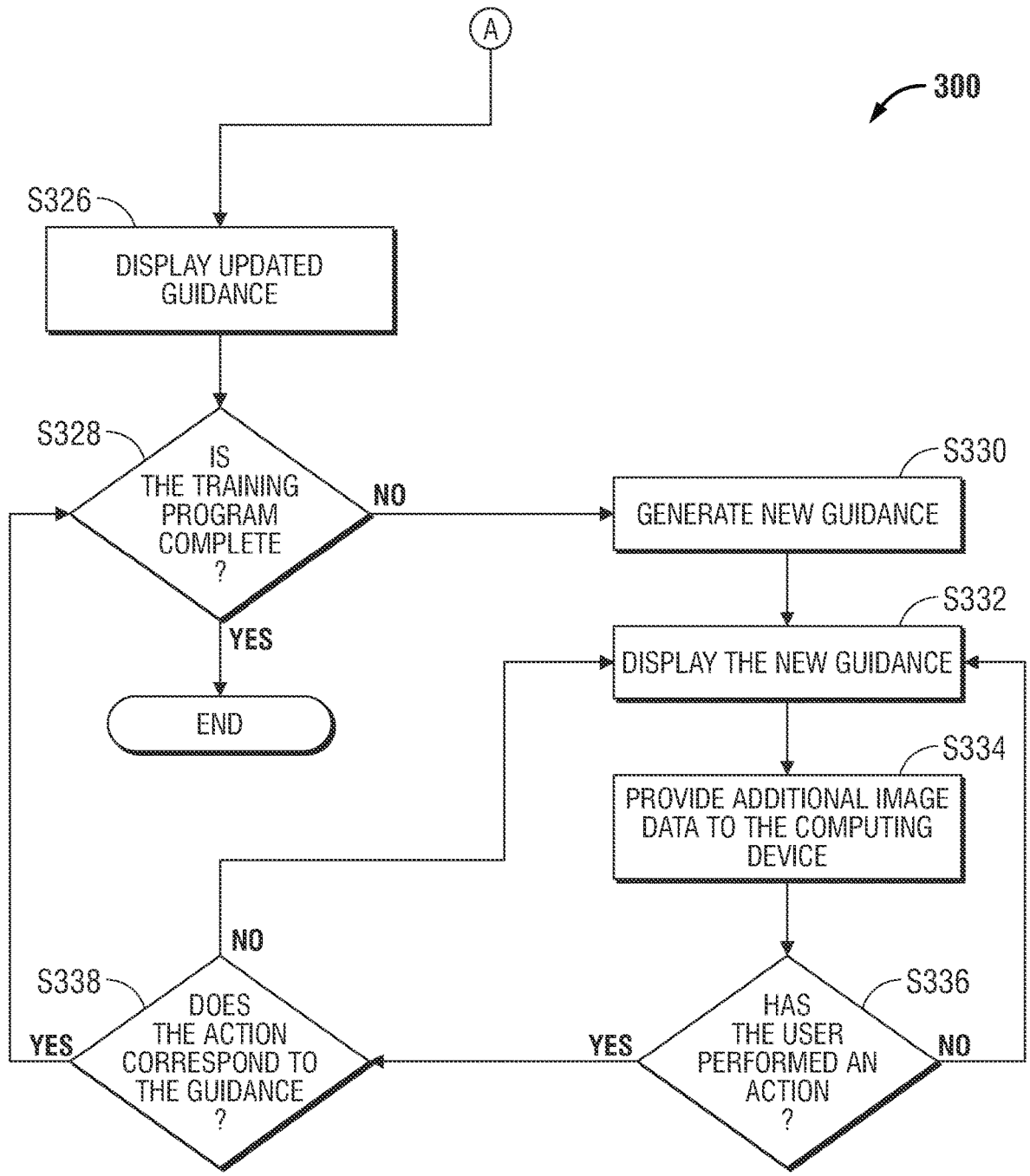

With reference to FIGS. 3A and 3B, there is shown a flowchart of an exemplary method 300 for providing guidance for positioning a body and a surgical robot, according to an embodiment of the present disclosure. In some embodiments, some or all of the steps of method 300 may be performed in a surgical operating environment, such as an operating room, prior to the start of a surgical procedure. In other embodiments, some or all of the steps of method 300 may be performed in an instructional or surgical training environment, such as a training facility where a curriculum is taught. Described below are various examples of using the various components of system 100 to perform the steps of method 300. However, those skilled in the art will recognize that some or all of these steps may be performed in a different order or sequence than what is described, repeated, omitted, or by using different components without departing from the scope of the present disclosure. In particular, while the examples provided below describe using HMD 120 as a display device, those skilled in the art will recognize that, as noted above, various other display devices, including one or more projectors, may also be used as the display device instead of, or in addition to, HMD 120 without departing from the scope of the present disclosure.

Starting at step S302, at least one image capture device 125 captures at least one image of the surgical training environment. As described above, the surgical training environment includes table 110 and surgical robot 150. In some embodiments, the surgical training environment may further include body B on table 110. Then, at step S304, image capture device 125 generates image data of the surgical training environment based on the captured image.

At step S306, computing device 200 receives at least one surgical training parameter. The surgical training parameter may be based on a training program. As noted above, database 240 stores various training programs including various surgical training parameters, including various types of surgery, types of patients, characteristics of the patients, and/or types of medical conditions being treated by the surgery. In embodiments, a user, such as a clinician, may select a training program and/or particular surgical training parameter via a GUI (for example a GUI generated based on GUI instructions 285), whereafter the training program and/or surgical training parameter is provided to computing device 200.

Thereafter, or concurrently therewith, at step S308, computing device 200 receives the image data of the surgical training environment from image capture device 125. In some embodiments, image capture device 125 does not generate the image data of the surgical training environment, but instead transmits the captured image to computing device 200, which in turn generates the image data of the surgical training environment based on the captured image. In such embodiments, it is the captured image that is received at step S308 and not the image data of the surgical training environment.

Next, at step S310, computing device 200 processes the image data to detect a pose of table 110 and/or surgical robot 150 based on the image data. For example, computing device 200 may perform various image processing and/or modelling techniques to identify various objects, including table 110 and surgical robot 150, in the image data. Computing device 200 then, at step S312, generates a virtual training environment based on the image data of the surgical training environment and the detected pose of table 110 and/or surgical robot 150. The virtual training environment may include, in some examples, a virtual representation of table 110 and/or surgical robot 150.

Computing device 200 then, at step S314, determines a pose of the user relative to the surgical training environment. The determination may be based on the received image data and/or the generated virtual training environment. For example, computing device 200 may utilize various image processing and/or object detection algorithms known to those skilled in the art to further process and analyze the image data received from image capture device 125 to identify the user in the image data. In embodiments, the user is identified in the image data relative to table 110 and/or surgical robot 150. Computing device 200 then determines a pose of the user relative to table 110 and/or surgical robot 150, and generates a representation of the user in the virtual training environment based on the determined pose of the user relative to table 110 and/or surgical robot 150. Computing device 200 may further augment the virtual training environment based on the determined pose of the user, thereby including a representation of the user in the virtual training environment.

Thereafter, at step S316, computing device 200 generates guidance for positioning body B on table 110 based on the surgical training parameter received at step S306 and the pose of the user relative to the surgical training environment determined at step S314. The guidance includes at least one command for positioning body B on table 110. For example, the guidance may include textual commands, graphical or other visual commands such as virtual and/or augmented reality images, and/or auditory commands. In embodiments, the guidance may include commands instructing the user to perform a particular action, such as to reposition one or more portions of body B into a recommended position. For example, the guidance may include commands displayed via augmented reality images of a recommended position into which body B should be placed. In some embodiments, the guidance may include multiple commands, and the commands may be provided in an ordered sequence.

The guidance may further include virtual and/or augmented reality images of body B on table 110 and a position of one or more organs or other internal structures inside body B. The position of the one or more organs or other internal structures may be based on a model of positions of organs and/or internal structures inside a body, and/or a scan of an actual patient's body. In some embodiments, the virtual and/or augmented reality images of the position of one or more organs or other internal structures inside body B include images of the skin of body B "peeling away" to reveal the one or more organs or other internal structures.

In embodiments, the guidance may be based on the surgical training parameter and/or training program received at step S306 and the virtual training environment generated at step S310. For example, computing device 200 may analyze the pose of body B and/or surgical robot 150, and the user's pose relative to body B and surgical robot 150, and generate the guidance based on the commands included in the training program, as modified based on the particular pose of body B and surgical robot 150 in the surgical training environment.

Computing device 200 generates further guidance for positioning surgical robot 150 about body B on table 110 and/or for adjusting the pose of surgical robot 150 into a recommended pose, based on the surgical training parameter received at step S306 and the pose of the user relative to the surgical training environment determined at step S314. Similar to the guidance for positioning body B upon table 110 as described above, the guidance for positioning surgical robot 150 about body B and/or adjusting the pose of surgical robot 150 may include various commands instructing the user to perform one or more actions. For example, the guidance may include textual commands, graphical or other visual commands such as virtual and/or augmented reality images, and/or auditory commands. In embodiments, the guidance may include commands displayed via augmented reality images of a recommended position into which surgical robot 150 should be placed and/or a recommended pose to which surgical robot 150 should be adjusted.

Computing device 200 then, at step S318, causes HMD 120 to display the generated guidance. Computing device 200 may further cause HMD 120 to display augmented reality images of a position of one or more organs or other internal structures of body B. The augmented reality images may be superimposed onto body B.

After displaying the guidance, computing device 200, at step S320, receives additional image data of the surgical training environment from image capture device 125. For example, as the user acts on the displayed guidance by performing the one or more actions required to satisfy a command, image capture device 125 may capture at least one additional image and process the additional image to generate additional image data, which is then transmitted to computing device 200.

Computing device 200 then, at step S322, processes and/or analyzes the additional image data to identify the action performed by the user, and determine whether the user has performed the all actions necessary to satisfy the command included in the guidance. For example, the actions may be movements performed by the user to move or reposition all or one or more portions (e.g. robotic arm 155) of surgical robot 150, and/or all or one or more portions (e.g. an arm, leg, torso, etc.) of body B. For example, computing device 200 may analyze the additional image data to detect a movement of the user, such as movement of the user's arms and/or hands, relative to the surgical training environment, and particularly table 110 and/or surgical robot 150, to determine if the user has performed a particular action indicated by the guidance. If computing device 200 determines that the user has performed an action ("Yes" at S322), processing proceeds to step S324. Alternatively, if computing device 200 cannot detect a movement of the user ("No" at S322), processing returns to step S318.

At step S324, computing device 200 determines whether the action that was performed by the user and identified at S322 corresponds to the guidance that was displayed at S318. For example, computing device 200 may then determine, based on the detected movement of the user, whether the user has performed the action indicated by the guidance that was displayed at step S318 to satisfy the command. Computing device 200 may further determine a training score assessed based on the user's performance of the action indicated by the command. For example, the training score assessment may be based on the precision, speed, consistency, etc. of the user's performance of the action indicated by the command. If computing device 200 determines that the action performed by the user does not correspond to the guidance ("No" at step S324), processing returns to step S318.

Alternatively, if computing device 200 determines that the action performed by the user corresponds to the guidance ("Yes" at step S324), processing proceeds to step S326, where computing device 200 generates and causes HMD 120 to display updated guidance indicating whether the user has satisfied the command. For example, computing device may cause HMD 120 to display an augmented reality image indicating the status of the command, e.g., whether the command has been satisfied, a degree of accuracy with which the user's actions satisfied the command, and/or the training score assessed based on the user's performance of the action indicated by the command.

Thereafter, at step S328, computing device 200 determines whether the training program has been completed. For example, if all of the actions required by the commands included in the guidance have been performed, computing device 200 may determine that the training program has been completed. If computing device 200 determines that the training program has been completed ("Yes" at step S328), computing device 200 causes HMD 120 to display a final score of the user, whereafter processing will end. Alternatively, if computing device 200 determines that the training program has not been completed ("No" at step S328), processing proceeds to step S330.

At step S330, computing device 200 generates new guidance for positioning body B on table 110, positioning surgical robot 150 about the surgical training environment, and/or adjusting the pose of surgical robot 150. For example, the new guidance may include an additional action to be performed by the user after the action required by the command included in the guidance generated at step S316 has been performed. In embodiments, the new guidance may include one or more commands instructing the user to perform a next step or phase of the training program, as described above. For example, the new guidance may include one or more commands instructing the user to reposition a different portion of body B and/or a different portion of surgical robot 150.

Thereafter, processing proceeds to step S332, where computing device 200 causes HMD 120 to display the generated new guidance. Computing device 200 further causes HMD 120 to also display the augmented reality image of a position of one or more organs or other internal structures of body B.

After displaying the guidance, computing device 200, at step S334, receives additional image data of the surgical training environment from image capture device 125. Computing device 200 then, at step S336, processes and/or analyzes the additional image data to identify an action performed by the user, and determine whether the action performed by the user satisfies a command included in the new guidance. For example, computing device 200 may analyze the additional image data to detect a movement of the user, such as movement of the user's arms and/or hands, relative to the surgical training environment, and particularly table 110 and/or surgical robot 150. If computing device 200 determines that the user has performed an action ("Yes" at step S336), processing proceeds to step S338. Alternatively, if computing device cannot detect a movement of the user ("No" at step S336), processing returns to step S332.

At step S338, computing device 200 determines whether the action that was performed by the user and identified at step S334 corresponds to a command included in the new guidance. For example, computing device 200 may determine, based on the detected movement of the user, whether the user has performed the action indicated by the guidance to satisfy the command. Computing device 200 further determines a training score assessed based on the user's performance of the action indicated by the command. If computing device 200 determines that the action performed by the user does not correspond to the guidance ("No" at step S338), processing returns to step S332. Alternatively, if computing device 200 determines that the action performed by the user and identified at step S334 corresponds to the new guidance displayed at step S332 ("Yes" at step S338), processing returns to step S328, where computing device 200 again determines whether the training program has been completed, and method 300 continues as described above with reference to step S328.

While the description above relating to method 300 of FIG. 3 refers to functions being performed by computing device 200, those skilled in the art will understand that such functions may be performed by computing device 200 based on execution of one or more applications, such as application 280, and/or based on dedicated hardware and/or other software included in computing device 200. Thus, while described as being performed by computing device 200, the description of method 300 should not be interpreted as being limited to hardware embodiments.

Figure 4A:
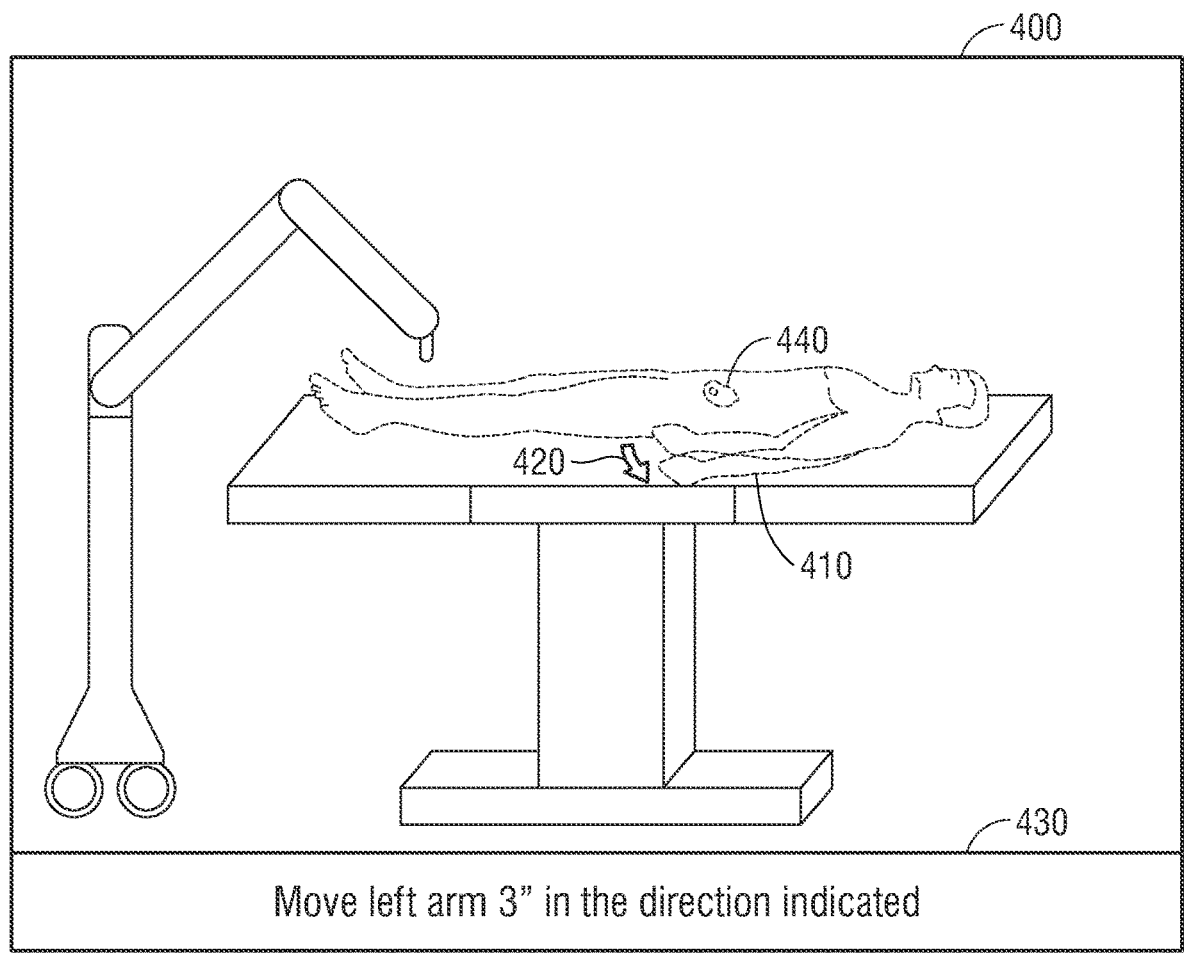
FIG. 4A shows an exemplary graphical user interface which may be displayed by a head-mounted display device forming part of the system of FIG. 1, according to an embodiment of the present disclosure.
Figure 4B:
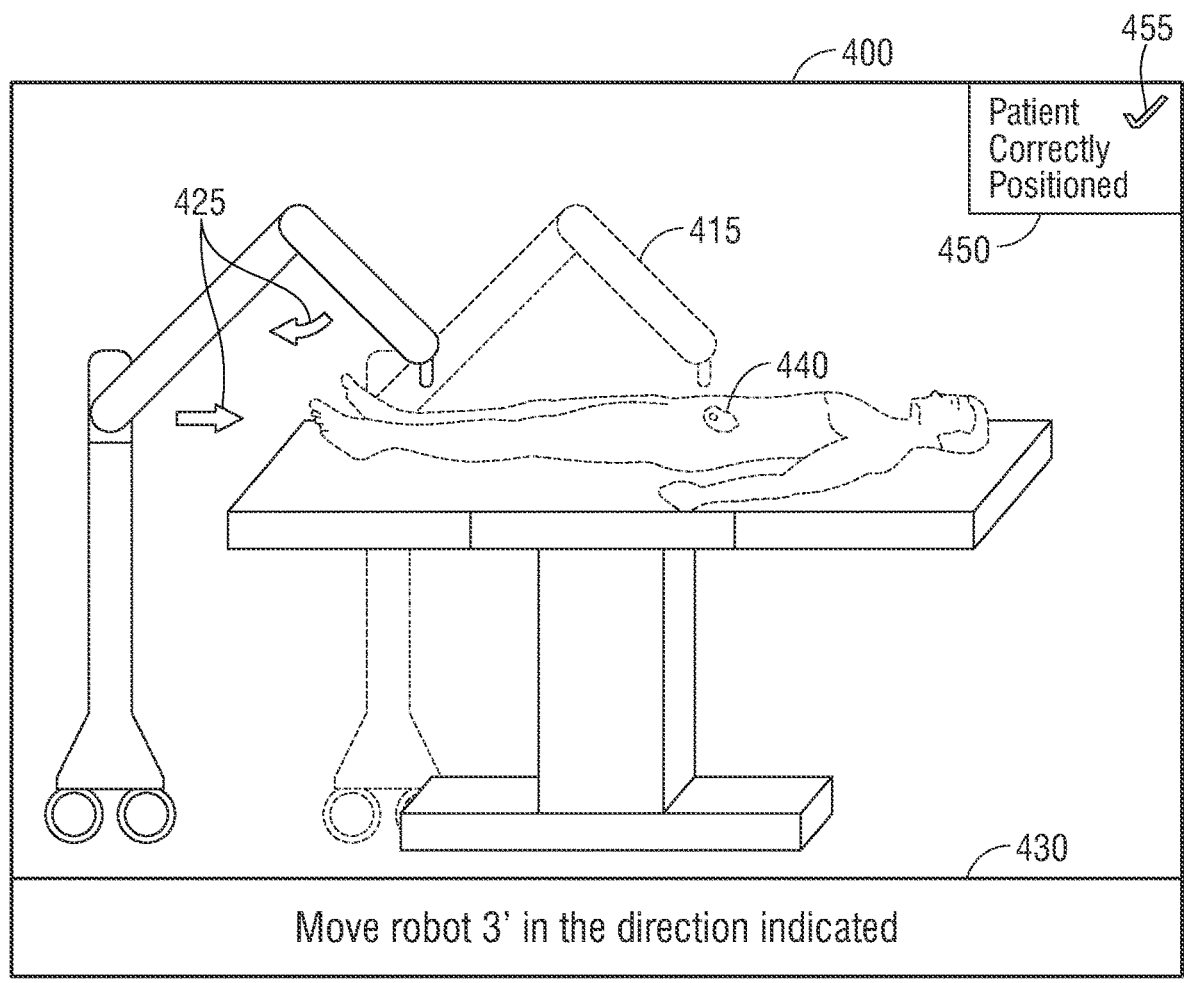
FIG. 4B shows another exemplary graphical user interface which may be displayed by a head-mounted display device forming part of the system of FIG. 1, according to an embodiment of the present disclosure.

Turning now to FIGS. 4A and 4B, there is shown an exemplary graphical user interface (GUI) 400 that may be displayed by HMD 120, according to an embodiment of the present disclosure. GUI 400 may be displayed by HMD 120 at various points during a surgical preparation and/or training procedure, such as the procedure described above with reference to method 300 of FIGS. 3A and 3B. In the embodiment demonstrated in FIG. 4A, table 110 and surgical robot 150 are physical objects in the surgical training environment visible to the user. Body B is shown lying on table 110. In this example, body B is a virtual body, and the guidance is instructing the user to move a left arm of body B three inches in a particular direction. The position into which the left arm of body B should be moved is indicated by a ghosted overlay 410 displayed onto body B. A directional indicator, such as an arrow 420, shows the direction into which the left arm of body B should be moved. The command is also displayed as textual instructions 430. Further, an augmented reality image of one or more organs 440 is shown overlaid and/or superimposed onto body B. In addition to the augmented reality image of one or more organs 440, GUI 400 may similarly include a graphical representation of the surgical site (not shown), and/or graphical representations of the recommended positions of surgical ports (not shown), as is further described in commonly-owned U.S. Patent Application No. 62/615,481, filed on Jan. 10, 2018 by Covidien LP, the entire contents of which are incorporated herein by reference.

After the user moves the left arm of body B into the indicated position, GUI 400 may be updated, as shown in FIG. 4B. GUI 400 may then show a confirmation image 450 indicating that body B has been correctly positioned. An indicator 455 may also be shown to inform the user that an action satisfying the command has been successfully performed. GUI 400 may also show the next command in the training program, for example, a command to reposition surgical robot 150. GUI 400 may show a ghosted image 415 of surgical robot 150 in the position and pose where surgical robot 150 should be positioned. Directional indicators, such as arrows 425, may also be shown indicating the direction into which surgical robot 150 and/or robotic arm 155 should be moved. The textual instructions 430 may also be updated based on the new command.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure.

What is claimed is:

1. A system for providing guidance for positioning a body and a surgical robot, the system comprising:
    an image capture device configured to:
        capture an image of a surgical environment including a table and a surgical robot; and
        generate image data of the surgical environment based on the captured image;
    a virtual display operable by a user; and
    a computing device including a processor and a memory storing instructions which, when executed by the processor, cause the computing device to:
        receive a surgical parameter;
        receive the image data of the surgical environment from the image capture device;
        detect a pose of the table and the surgical robot based on the received image data;
        generate a virtual environment based on the image data of the surgical environment, the virtual environment including representations of the table and the surgical robot;
        determine a pose of the user relative to the surgical environment based on the received image data and the generated virtual environment;
        generate guidance for positioning at least one of at least a portion of a body on the table or at least a portion of the surgical robot about the body, based on the surgical parameter and the determined pose of the user operating the virtual display relative to the surgical environment; and
        cause the virtual display to display the generated guidance.

2. The system according to claim 1, wherein the body is a mannequin, and the surgical environment further includes the body on the table, and wherein the guidance includes a command for positioning at least a portion of the body on the table based on the surgical parameter.

3. The system according to claim 2, wherein the command includes a textual command displayed by the virtual display.

4. The system according to claim 3, wherein the computing device causes the virtual display to display an augmented reality image of a position of at least one organ of the body as superimposed onto the body.

5. The system according to claim 2, wherein the command includes an augmented reality image of a recommended position into which at least a portion of the body should be placed.

6. The system according to claim 5, wherein the guidance indicates when the user has placed at least a portion of the body into the recommended position.

7. The system according to claim 2, wherein the guidance includes an augmented reality image of a position of at least one organ of the body.

8. The system according to claim 7, wherein the augmented reality image of the position of the at least one organ of the body is based on a model of positions of organs inside a patient's body.

9. The system according to claim 2, wherein the command includes an augmented reality image of a recommended position into which at least a portion of the surgical robot should be placed.

10. The system according to claim 1, wherein the virtual environment further includes a representation of a virtual body.

11. The system according to claim 1, wherein the image capture device is coupled to the virtual display, and wherein the virtual display is a head mounted display (HMD).

12. The system according to claim 1, wherein the image capture device is one of a plurality of image capture devices, and wherein the plurality of image capture devices are positioned at a plurality of respective positions about the surgical environment.

13. The system according to claim 1, wherein receiving the surgical parameter includes loading a preconfigured surgical parameter from the memory.

14. The system according to claim 1, wherein receiving the surgical parameter includes receiving a selection of a surgical parameter from input by the user.

15. The system according to claim 1, wherein the surgical parameter is a surgical training parameter based on a training program.

16. The system according to claim 1, wherein the surgical parameter includes one or more of:
    a type of surgery;
    an age of a patient;
    a weight of the patient;
    a size of the patient; and
    a medical condition of the patient.

17. The system according to claim 1, wherein the instructions for causing the computing device to determine a pose of the user operating the virtual display relative to the surgical environment includes further instructions which, when executed by the processor, cause the computing device to:
    analyze the received image data to identify the user and one or more of the table and the surgical robot in the received image data;
    determine a position of the user relative to one or more of the table and the surgical robot; and
    generate a representation of the user in the virtual environment based on the determined position of the user relative to one or more of the table or the surgical robot.

18. A system for providing guidance for positioning a body and a surgical robot, the system comprising:
    an image capture device configured to:
        capture an image of a surgical environment including a table and a surgical robot; and generate image data of the surgical environment based on the captured image;

a virtual display operable by a user; and a computing device including a processor and a memory storing instructions which, when executed by the processor, cause the computing device to:

receive a surgical parameter by at least one of loading a preconfigured surgical parameter from the memory or receiving a selection of a surgical parameter from input by the user;

receive the image data of the surgical environment from the image capture device;

detect a pose of the table and the surgical robot based on the received image data; and generate a virtual environment based on the image data of the surgical environment, the virtual environment including representations of the table and the surgical robot.

19. The system according to claim 18, wherein the computing device is further configured to:

determine a pose of the user relative to the surgical environment based on the received image data and the generated virtual environment;

generate guidance for positioning at least one of at least a portion of a body on the table or at least a portion of the surgical robot about the body, based on the surgical parameter and the determined pose of the user operating the virtual display relative to the surgical environment; and cause the virtual display to display the generated guidance.

20. The system according to claim 19, wherein the instructions for causing the computing device to determine a pose of the user operating the virtual display relative to the surgical environment includes further instructions which, when executed by the processor, cause the computing device to:

analyze the received image data to identify the user and one or more of the table and the surgical robot in the received image data;

determine a position of the user relative to one or more of the table and the surgical robot; and generate a representation of the user in the virtual environment based on the determined position of the user relative to one or more of the table or the surgical robot.

* * * * *